(12) United States Patent
Nakajima et al.

(10) Patent No.: US 12,089,947 B2
(45) Date of Patent: Sep. 17, 2024

(54) COGNITIVE FUNCTION EVALUATION DEVICE, COGNITIVE FUNCTION EVALUATION SYSTEM, AND RECORDING MEDIUM

(71) Applicant: Panasonic Intellectual Property Management Co., Ltd., Osaka (JP)

(72) Inventors: Hirobumi Nakajima, Kyoto (JP); Kengo Abe, Nara (JP); Takashi Nishiyama, Hyogo (JP); Yoshihiro Matsumura, Osaka (JP); Sadayuki Sumi, Hyogo (JP); Kohji Sasabe, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 1015 days.

(21) Appl. No.: 16/955,132

(22) PCT Filed: Nov. 28, 2018

(86) PCT No.: PCT/JP2018/043686
§ 371 (c)(1),
(2) Date: Jun. 18, 2020

(87) PCT Pub. No.: WO2019/130957
PCT Pub. Date: Jul. 4, 2019

(65) Prior Publication Data
US 2020/0315519 A1    Oct. 8, 2020

(30) Foreign Application Priority Data

Dec. 27, 2017  (JP) .................................. 2017-251177

(51) Int. Cl.
G16H 50/20    (2018.01)
A61B 5/00    (2006.01)
(Continued)

(52) U.S. Cl.
CPC .......... *A61B 5/4088* (2013.01); *A61B 5/1113* (2013.01); *A61B 5/6891* (2013.01);
(Continued)

(58) Field of Classification Search
None
See application file for complete search history.

(56) References Cited

U.S. PATENT DOCUMENTS

| 6,796,799 B1 | 9/2004 | Yoshiike | |
| 2005/0278409 A1* | 12/2005 | Kutzik | G16H 50/30 709/200 |

(Continued)

FOREIGN PATENT DOCUMENTS

| CN | 105242600 A | 1/2016 |
| JP | 2000237098 A | 9/2000 |

(Continued)

OTHER PUBLICATIONS

Abe et al, Early Detection System of Senile Dementia by Behavior Sensing, 2013 IEEE 17th International Symposium on Consumer Electronics (ISCE) (Year: 2013).*
(Continued)

*Primary Examiner* — Gregory Lultschik
(74) *Attorney, Agent, or Firm* — Renner, Otto, Boisselle & Sklar, LLP (57) ABSTRACT

A cognitive function evaluation device includes: an obtainment unit that obtains use information indicating a state of use of a toilet by a subject; a calculation unit that calculates a total number of times of use of a toilet by the subject, based on the use information obtained by the obtainment unit; an evaluation unit that evaluates a cognitive function of the subject, based on the total number of times of use calculated by the calculation unit; and an output unit that outputs a result of evaluation performed by the evaluation unit.

4 Claims, 9 Drawing Sheets

(51) Int. Cl.
    *A61B 5/11*           (2006.01)
    *E03D 9/00*          (2006.01)
    *G16H 20/70*         (2018.01)
    *G16H 50/30*        (2018.01)

(52) U.S. Cl.
    CPC .............. *E03D 9/00* (2013.01); *G16H 20/70* (2018.01); *G16H 50/20* (2018.01); *G16H 50/30* (2018.01)

(56) References Cited

U.S. PATENT DOCUMENTS

| | | |
|---|---|---|
| 2008/0084296 A1 | 4/2008 | Kutzik et al. |
| 2013/0132110 A1 | 5/2013 | Nagaoka |
| 2014/0324470 A1 | 10/2014 | Hatano |
| 2017/0095193 A1 | 4/2017 | Shin et al. |
| 2017/0365149 A1 | 12/2017 | Ten Kate |
| 2018/0032693 A1* | 2/2018 | Schuurkamp .......... A61B 5/743 |

FOREIGN PATENT DOCUMENTS

| | | |
|---|---|---|
| JP | 2001-34869 A | 2/2001 |
| JP | 2006-236128 A | 9/2006 |
| JP | 2009-282879 A | 12/2009 |
| JP | 2010-220761 A | 10/2010 |
| JP | 2012-190294 A | 10/2012 |
| JP | 2013-109661 A | 6/2013 |
| JP | 2013-182470 A | 9/2013 |
| JP | 2016-173732 A | 9/2016 |
| JP | 2017-167878 A | 9/2017 |
| WO | 2013/065864 A1 | 5/2013 |
| WO | 2017/170831 A1 | 10/2017 |

OTHER PUBLICATIONS

International Search Report and Written Opinion for corresponding Application No. PCT/JP2018/043686, mailed Feb. 26, 2019.
Office Action dated Sep. 28, 2022 for corresponding Chinese Patent Application No. 201880083581.6.
Translation of the Search Report accompanying the Office Action dated Sep. 28, 2022 for corresponding Chinese Patent Application 201880083581.6.
Chinese Office Action for corresponding Chinese Patent Application No. 201880083581.6, issued Jun. 17, 2023.
Chinese Search Report accompanying the Office Action for corresponding Chinese Patent Application 201880083581.6, issued Jun. 17, 2023, with English translation.
Chinese Office Action for corresponding Chinese Patent Application No. 201880083581.6, issued Dec. 22, 2023.
Chinese Search Report accompanying the Office Action for corresponding Chinese Patent Application 201880083581.6, issued Dec. 22, 2023, with English translation.

* cited by examiner

| No. | SCORE | DETERMINATION |
|---|---|---|
| 403 | 15 | HEALTHY |
| 406 | 14 | HEALTHY |
| 501 | 14 | HEALTHY |
| 505 | 14 | HEALTHY |
| 405 | 12 | MCI |
| 507 | 12 | MCI |
| 510 | 11 | MCI |
| 407 | 10 | MCI |
| 504 | 6 | DEMENTIA |
| 404 | 4 | DEMENTIA |
| 503 | 0 | DEMENTIA |

COGNITIVE FUNCTION EVALUATION DEVICE, COGNITIVE FUNCTION EVALUATION SYSTEM, AND RECORDING MEDIUM

TECHNICAL FIELD

The present invention relates to a cognitive function evaluation device, a cognitive function evaluation system, and a recording medium.

BACKGROUND ART

Conventionally, there have been devices that evaluate a cognitive function of a subject (see, for example, Patent Literature (PTL) 1).

PTL 1 discloses a device that includes a data base which stores evaluation contents of a plurality of evaluation items and case information, etc., in association with one another, derives an evaluation item, and derives the next evaluation item according to an input of an evaluation result of the subject for the derived evaluation item. According to the device described in PTL 1, it is possible to carry out evaluation with contents and an order according to an evaluation result of the subject for an evaluation instead of evaluation with predetermined contents and an order.

CITATION LIST

Patent Literature

PTL 1: International Publication No. 2013/065864

SUMMARY OF THE INVENTION

Technical Problem

In performing cognitive function evaluation, it is required to easily evaluate a cognitive function of a subject for the evaluation.

In view of the above, an object of the present invention is to provide a cognitive function evaluation device, etc. capable of easily evaluating a cognitive function of a subject for the evaluation.

Solutions to Problem

A cognitive function evaluation device according to one aspect of the present invention includes an obtainment unit configured to obtain use information indicating a state of use of a toilet by a subject; a calculation unit configured to calculate a total number of times of use of a toilet by the subject, based on the use information obtained by the obtainment unit; an evaluation unit configured to evaluate a cognitive function of the subject, based on the total number of times of use calculated by the calculation unit; and an output unit configured to output a result of evaluation performed by the evaluation unit.

In addition, a cognitive function evaluation system according to one aspect of the present invention includes: the cognitive function evaluation device described above; and a detection device that detects the use information indicating the state of use of the toilet by the subject, and outputs the use information to the obtainment unit included in the cognitive function evaluation device.

In addition, a recording medium according to one aspect of the present invention is a non-transitory computer-readable recording medium for use in a computer, the recording medium having a computer program recorded thereon for causing the computer to execute a cognitive function evaluation method, the cognitive function evaluation method including: obtaining use information indicating a state of use of a toilet by a subject; calculating a total number of times of use of a toilet by the subject, based on the use information obtained in the obtaining; evaluating a cognitive function of the subject, based on the total number of times of use calculated in the calculating; and outputting a result of evaluation performed in the evaluating.

Advantageous Effect of Invention

With the cognitive function evaluation device according to the present invention, it is possible to easily evaluate a cognitive function of a subject.

DESCRIPTION OF EXEMPLARY EMBODIMENTS

Hereinafter, embodiments of the present invention will be described with reference to the drawings. It should be noted that each of the embodiments described below shows a general or specific example. The numerical values, shapes, materials, structural components, the arrangement and connection of the structural components, steps, the processing order of the steps, etc. shown in the following embodiments are mere examples, and therefore do not limit the scope of the appended claims and their equivalents. Therefore, among the structural components in the following embodiments, structural components not recited in any one of the independent claims are described as arbitrary structural components.

In addition, each of the diagrams is a schematic diagram and not necessarily strictly illustrated. Furthermore, in each of the diagrams, substantially the same structural components are assigned with the same reference signs, and redundant descriptions will be omitted or simplified in some cases.

Embodiment

[Configuration of Cognitive Function Evaluation Device]

Figure 1:
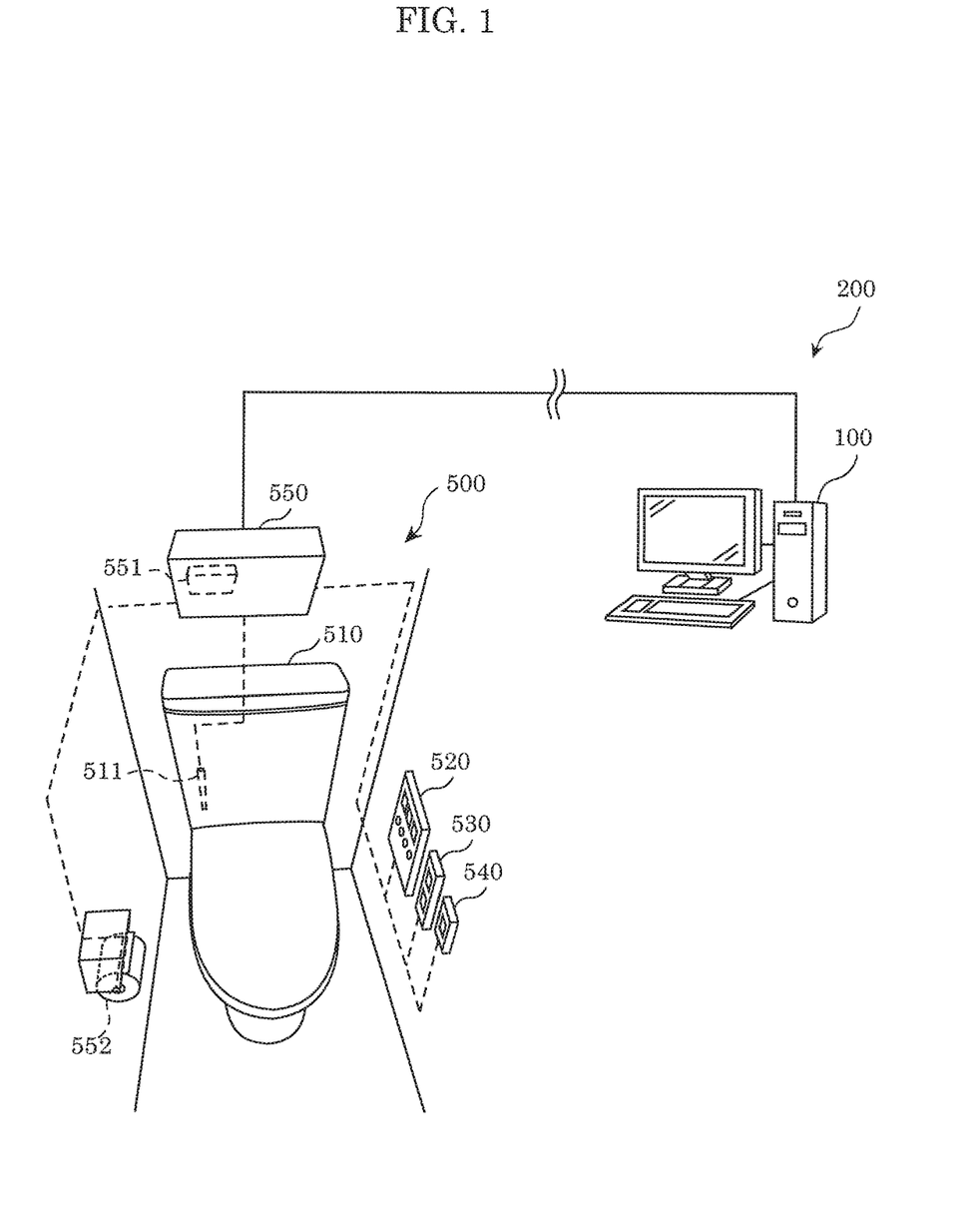
FIG. 1 is a diagram for explaining an outline of a cognitive function evaluation system according to an embodiment.
Figure 2:
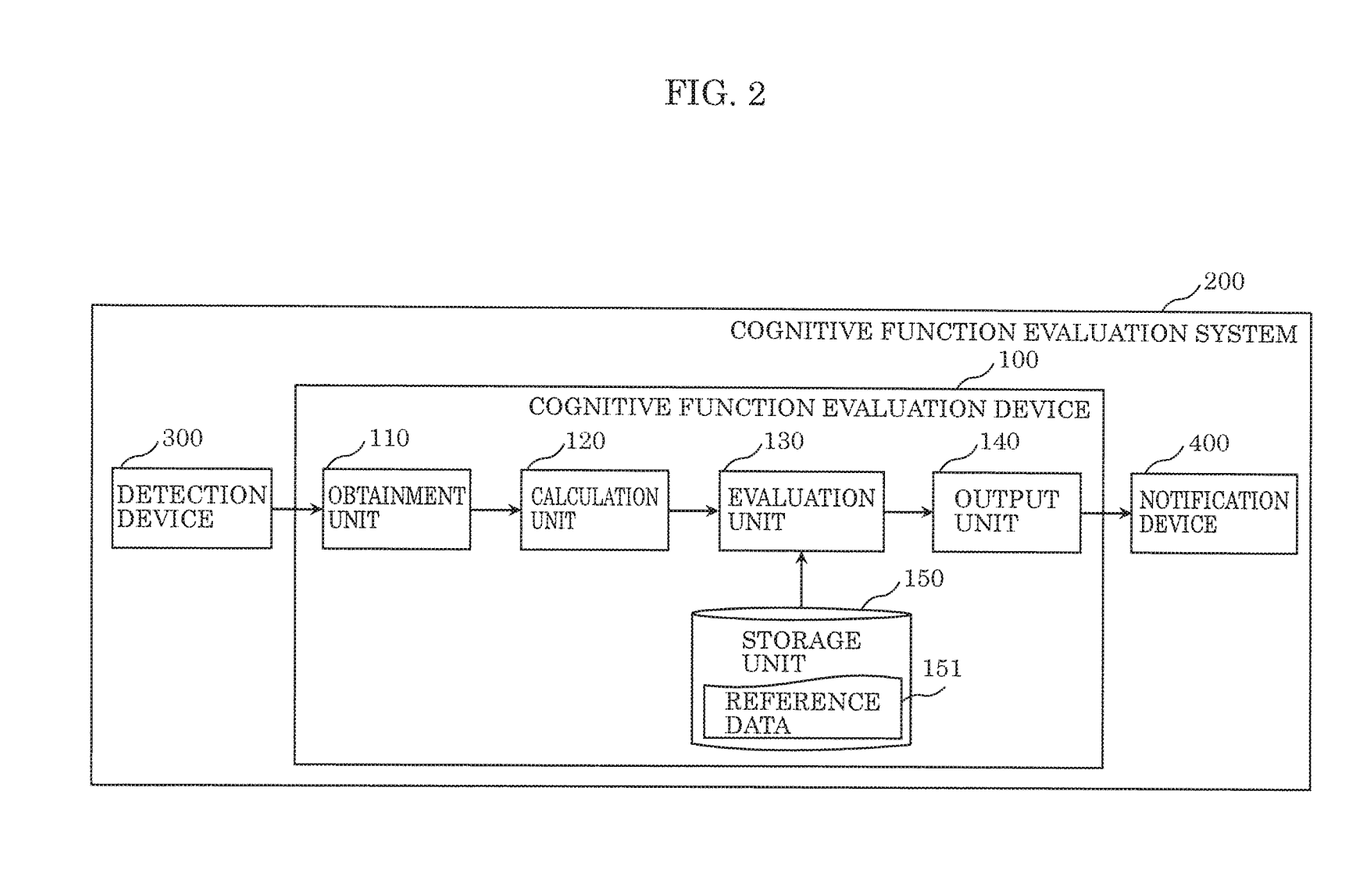
FIG. 2 is a block diagram illustrating a characteristic functional configuration of a cognitive function evaluation device and the cognitive function evaluation system according to the embodiment.

The following describes a configuration of a cognitive function evaluation system according to an embodiment. FIG. 1 is a diagram for explaining an outline of cognitive function evaluation system 200 according to the embodiment. FIG. 2 is a block diagram illustrating a characteristic functional configuration of cognitive function evaluation device 100 and cognitive function evaluation system 200 according to the embodiment.

Cognitive function evaluation system 200 is an apparatus for evaluating a degree of a cognitive function of a subject for cognitive function evaluation, based on a total number of times of use of a toilet by the subject. The cognitive function indicates a capability of recognizing, memorizing, or determining. As one specific example, cognitive function evaluation device 100 evaluates whether or not a subject is a person suspected of having a mild cognitive impairment (MCI) or dementia (an MCI patient or a dementia patient).

The dementia indicates a symptom of a decrease in the above-described cognitive functions. One specific example of the dementia is an Alzheimer's disease (AD). Since dementia is asymptomatic, a dementia patient will have an examination by a doctor by being urged to be examined at a hospital by a family member of the dementia patient, a third party, or the like. Alternatively, for example, a subject undergoes a batch test for diagnosis of dementia, such as "forgetfulness counseling program" (manufactured by Kodensha Co., Ltd.), thereby enabling confirming whether or not the subject has dementia. It should be noted that the MCI indicates a symptom of a decrease in a cognitive function to the degree involving no trouble in daily life, and the dementia indicates a symptom of a decrease in a cognitive function to the degree involving trouble in daily life.

However, with such a batch test for diagnosis of dementia, there is a problem that, for example, a subject memorizes test items after taking the batch test several times, leading to a decrease in accuracy of determining dementia. In addition, since the dementia is asymptomatic as described above, a subject may not have an examination by a doctor unless the subject is urged to be examined at a hospital by a family member of the dementia patient, a third party, or the like.

As a result of earnest investigation, the inventors of the present invention have found that there is a correlation between the total number of times of use of a toilet by a subject and the degree of a cognitive function of the subject.

As illustrated in FIG. 1, cognitive function evaluation device 100 is connected to, for example, distribution panel 550 in toilet 500.

Distribution panel 550 supplies power from an external utility power source which is not illustrated to electric devices in toilet 500. Distribution panel 550 is electrically connected to, for example, a heater (not illustrated) for adjusting a temperature of a toilet seat, a water temperature, etc. of toilet bowl 510, toilet device control button 520 including buttons for controlling the heater by a user of toilet 500, etc. In addition, distribution panel 550 is electrically connected, for example, to electric devices in toilet 500, such as drainage button 530 that includes, for example, a button or the like for draining water in toilet bowl 510, human detecting sensor 540 that detects whether a user is present in toilet 500, etc.

For example, distribution panel 550 includes electric power meter 551 that is for measuring power used in toilet 500, and is one example of detection device 300. Electric power meter 551 outputs an amount of electric power consumption that has been measured to obtainment unit 110 included in cognitive function evaluation device 100, as use information indicating a state of use of toilet 500 by the subject. The use information is, for example, information for causing cognitive function evaluation device 100 to determine whether or not the subject has used toilet 500. In addition, for example, distribution panel 550 obtains a total number of times of detection by human detecting sensor 540 that is another example of detection device 300 in toilet 500, and outputs the total number of times of detection that has been obtained, as use information, to obtainment unit 110 included in cognitive function evaluation device 100.

As illustrated in FIG. 2, cognitive function evaluation system 200 includes cognitive function evaluation device 100, detection device 300 that detects use information indicating a state of use of toilet 500 by a subject, and notification device 400.

Cognitive function evaluation device 100 is a computer that calculates the total number of times of use of toilet 500 by the subject during a predetermined period of time on the basis of the use information that has been detected by detection device 300 and indicates the state of use of toilet 500 by the subject, and evaluates the degree of a cognitive function of the subject. Cognitive function evaluation device 100, after evaluating the degree of the cognitive function of the subject, outputs a result of the evaluation to notification device 400. Notification device 400 notifies the subject, a family member of the subject, a private medical doctor of the subject, etc. of the result of the evaluation obtained from cognitive function evaluation device 100, by means of a sound, an image, or the like. It should be noted that the predetermined period of time that is set in advance may be arbitrarily set. For example, the predetermined period of time may be one day, one week, or one month.

Detection device 300 is a sensor that detects use information indicating a state of use of toilet 500 by a subject, and outputs the use information to obtainment unit 110 included in cognitive function evaluation device 100. Examples of detection device 300 include: electric power meter 551 that detects an amount of electric power consumption of toilet 500; water flowmeter 511 that detects an amount of water used in toilet 500; detection sensor 552 that detects an amount of toilet paper used in toilet 500; and human detecting sensor 540. It is sufficient for cognitive function evaluation system 200 to include, as detection device 300, at least one of electric power meter 551, water flowmeter 511, detection sensor 552, or human detecting sensor 540.

Electric power meter 551 is a measuring instrument that measures an amount of electric power consumption of each of the electric devices in toilet 500.

Water flowmeter 511 is a measuring instrument that measures an amount of water used in toilet 500. Water flowmeter 511 is disposed in a water tank in toilet bowl 510, for example, and detects a change in an amount of water in the water tank as use information. Water flowmeter 511 is, for example, an ultrasonic flowmeter, but not strictly limited as long as it is possible to measure an amount of water used in toilet 500.

Detection sensor 552 is a sensor for detecting an amount of toilet paper used. Detection sensor 552 may be, for example, a weight sensor that detects a weight of toilet paper, but not strictly limited as long as it is possible to measure an amount of toilet paper used.

Human detecting sensor 540 is a sensor that detects the presence or absence of a person in toilet 500. Human detecting sensor 540 is, for example, an infrared sensor, but not strictly limited as long as it is possible to detect the presence or absence of a person.

It should be noted that cognitive function evaluation system 200 may include, as detection device 300, two of more of electric power meter 551, water flowmeter 511, detection sensor 552, and human detecting sensor 540. Cognitive function evaluation device 100 is capable of increasing accuracy in the total number of times of use of toilet 500 by a subject that is calculated by calculation unit 120, by including multiple devices as detection device 300 capable of detecting use information.

Notification device 400 informs a subject, etc. of a result of evaluation output from cognitive function evaluation device 100, by means of a sound, an image, etc. Notification device 400 is, for example, a monitor including a liquid-crystal panel, an organic electroluminescence (EL) panel, or the like, a speaker, a television set, or an information terminal such as a smartphone, a tablet terminal, etc.

It is sufficient for cognitive function evaluation device 100, detection device 300, and notification device 400 to be capable of transmitting or receiving data indicating use information, a result of evaluation, etc., and may be connected in a wired manner or to be capable of performing radio communication.

It should be noted that cognitive function evaluation device 100 is, for example, a personal computer, but may be a server device.

As illustrated in FIG. 2, cognitive function evaluation device 100 includes obtainment unit 110, calculation unit 120, evaluation unit 130, output unit 140, and storage unit 150.

Obtainment unit 110 obtains use information indicating a state of use of toilet 500 by a subject. More specifically, obtainment unit 110 obtains the use information detected by detection device 300 from detection device 300. Obtainment unit 110 is, for example, an interface such as an adaptor, for connecting detection device 300 and cognitive function evaluation device 100.

In addition, obtainment unit 110 obtains, as use information of toilet 500 of the subject, an amount of electric power consumed in toilet 500, an amount of water used in toilet 500, an amount of toilet paper used in toilet 500, or the total number of times of detection by human detecting sensor 540 in toilet 500. Examples of detection device 300 include: electric power meter 551 that detects an amount of electric power consumption of toilet 500; water flowmeter 511 that detects an amount of water used in toilet 500; detection sensor 552 that detects an amount of toilet paper used in toilet 500; and human detecting sensor 540. Obtainment unit 110 obtains the use information detected by detection device 300.

Calculation unit 120 calculates the total number of times of use of toilet 500 by a subject, based on the use information obtained by obtainment unit 110. Calculation unit 120 may be implemented by software using a processor or a microcomputer, for example, or may be implemented by hardware using a dedicated circuit.

Evaluation unit 130 evaluates a cognitive function of a subject, based on the total number of times of use that has been calculated by calculation unit 120. More specifically, evaluation unit 130 checks the total number of times of use of toilet 500 by the subject that has been calculated by calculation unit 120 against reference data 151 stored in storage unit 150 to evaluate a cognitive function of the subject. For example, storage unit 150 stores, as reference data 151, a threshold of the total number of times of use of toilet 500 for distinguishing between a healthy subject and a mild cognitive impairment patient or a dementia patient. Evaluation unit 130 compares the total number of times of use of toilet 500 that has been calculated by calculation unit 120 with the threshold that is stored as reference data 151, and thereby evaluates whether the subject is a healthy subject, or a mild cognitive impairment patient or a dementia patient. Evaluation unit 130 may be implemented by software using a processor or a microcomputer, for example, or may be implemented by hardware using a dedicated circuit. It should be noted that calculation unit 120 and evaluation unit 130 may be implemented by a processor, a microcomputer, or a dedicated circuit that has the functions of both calculation unit 120 and evaluation unit 130, or may be implemented by a combination of two or more of the processor, the microcomputer, and the dedicated circuit.

In addition, for example, evaluation unit 130 evaluates a cognitive function of a subject whose total number of times of use of toilet 500 is lower than or equal to a predetermined threshold, to be lower than a cognitive function of a subject whose total number of times of use of toilet 500 is higher (i.e., a greater number of times of use) than the predetermined threshold.

Output unit 140 outputs, to notification device 400, a result of evaluation of the degree of the cognitive function of the subject which has been performed by evaluation unit 130. Output unit 140 is, for example, a communication interface such as a communication adaptor for connecting notification device 400 and cognitive function evaluation device 100.

Storage unit 150 is a storage device in which reference data 151 that indicates a relationship between the total number of times of use of toilet 500 by a person and a cognitive function of the person is stored. Reference data 151 is data that is stored in advance in storage unit 150, and is referred to by evaluation unit 130 when the cognitive function of a subject is evaluated. In other words, evaluation unit 130 evaluates a cognitive function of the subject by checking the total number of times of use of toilet 500 by the subject calculated by calculation unit 120 against reference data 151 stored in storage unit 150. Storage unit 150 is implemented by, for example, a read only memory (ROM), a non-volatile random access memory (RAM), etc.

In addition, a program that is executed by calculation unit 120 and evaluation unit 130, and image data and/or sound data indicating a result of evaluation that is used when outputting the result of evaluation of the cognitive function of the subject are also stored in storage unit 150.

[Processing Procedure of Cognitive Function Evaluation Device]

The following describes a specific processing procedure of a cognitive function evaluation method performed by cognitive function evaluation device 100.

Figure 3:
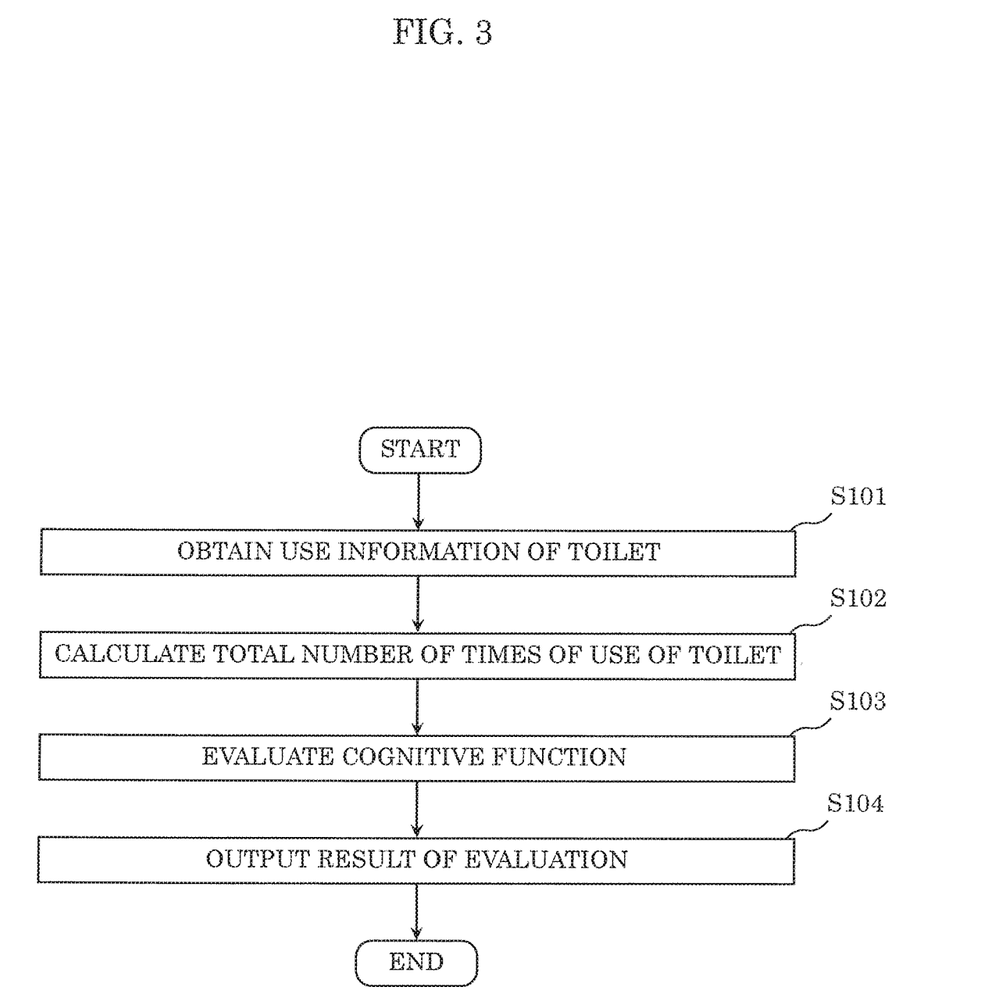
FIG. 3 is a flowchart illustrating a processing procedure for evaluating a cognitive function of a subject by the cognitive function evaluation device according to the embodiment.

FIG. 3 is a flowchart illustrating a processing procedure of evaluating a cognitive function of a subject performed by cognitive function evaluation device 100 according to the embodiment.

First, obtainment unit 110 obtains use information that is detected by detection device 300 and indicates a state of use of toilet 500 by a subject (Step S101). In Step S101, for example, when detection device 300 is an electric power meter, obtainment unit 110 obtains an amount of electric power consumed in toilet 500 from detection device 300. It should be noted that, when toilet 500 is used by a plurality of persons, an authentication device for identifying a subject may be disposed in toilet 500. The authentication device includes, for example, a camera for performing retina authentication, fingerprint authentication, etc., and a memory that stores information for performing the authentication, such as information of a retina, a fingerprint, etc., of a subject. The authentication device identifies, by the camera, a subject who uses toilet 500, and transmits information for identifying the subject to cognitive function evaluation device 100 or detection device 300. In this manner, cognitive function evaluation device 100 is capable of more accurately calculating an amount of electric power consumption when toilet 500 is used by the subject.

Next, calculation unit 120 calculates the total number of times of use of toilet 500 by the subject, based on the use information obtained in Step S101 (Step S102). In Step S102, for example, when detection device 300 is electric power meter 551, calculation unit 120 may obtain a change in the amount of electric power consumption. Calculation unit 120, may determine that the subject has used toilet 500 when, for example, the amount of electric power consumption has rapidly changed.

In addition, storage unit 150 may store, for example, an estimated value of the amount of electric power consumption per a single use of toilet 500 by the subject. In this case, calculation unit 120 may calculate the total number of times of use of toilet 500 by the subject per day, based on, for example, the estimated value and a total amount of electric power consumption per day.

In the same manner as above, when detection device 300 is water flowmeter 511 or detection sensor 552 that detects the amount of toilet paper used, calculation unit 120 may obtain a change in the amount of the corresponding item, and determine that the subject has used toilet 500 when the amount of the corresponding item has rapidly changed. Alternatively, storage unit 150 may store in advance an estimated value of the amount of use of each item per day, and calculation unit 120 may calculate the total number of times of use of toilet 500 by the subject per day, based on the estimated value and a total amount of use of the item per a single use. In addition, when detection device 300 is human detecting sensor 540, calculation unit 120 may calculate the total number of times of use of toilet 500 by the subject per day, based on, for example, a total number of times of detection by human detecting sensor 540.

Next, evaluation unit 130 evaluates a cognitive function of the subject, based on the total number of times of use that has been calculated in Step S102 (Step S103). In Step S103, evaluation unit 130 evaluates a cognitive function of a subject whose total number of times of use of toilet 500 is lower than or equal to a predetermined threshold to be lower than a subject whose total number of times of use of toilet 500 is higher than the predetermined threshold. More specifically, evaluation unit 130 evaluate the degree of the cognitive function of the subject, by checking the total number of times of use of toilet 500 by the subject that has been calculated by calculation unit 120 against reference data 151 that is a threshold stored in storage unit 150.

Finally, output unit 140 outputs a result of evaluation performed by evaluation unit 130 in Step S103 (Step S104). For example, when notification device 400 is a monitor device, and the result of evaluation output in Step S104 is image data, notification device 400 obtains the result of evaluation and displays the image data.

As described above, the cognitive function evaluation method performed by cognitive function evaluation device 100 includes: an obtaining step in which use information that indicates a state of use of toilet 500 by a subject is obtained (Step S101); a calculating step in which a total number of times of use of toilet 500 by the subject is calculated based on the use information obtained in the obtaining step (Step S102); an evaluating steps in which a cognitive function of the subject is evaluated based on the total number of times of use calculated in the calculating step (Step S103); and an outputting step in which a result of the evaluation performed in the evaluating step is output (Step S104).

It should be noted that, in Step S104, output unit 140 may output, to notification device 400, a result of evaluation only when evaluation unit 130 has determined that the subject is in a state of having a decreased cognitive function (i.e., having a mild cognitive impairment or dementia) in Step S103. In this manner, output unit 140 is capable of informing a subject, a family member of the subject, etc. of the result of evaluation only in the case of particular importance where a diagnosis of a doctor is considered to be necessary.

[Details of Reference Data]

In the following, the details of reference data 151 will be described. A threshold of a total number of times of use of toilet 500 is sufficient as reference data 151 to be used by evaluation unit 130 for determining whether a subject is a healthy subject or not. In addition, the use information may be, for example, an amount of electric power consumed in toilet 500, an amount of water used in toilet 500, or a total number of times of detection by human detecting sensor 540. In the following, the case where electric power meter 551 is employed as detection device 300 will be described.

By the way, in a diagnosis of dementia, a person undergoes a forgetfulness counseling program that is a batch test for a diagnosis of dementia, and thereby it is possible to determine whether the person has dementia.

Figure 4:
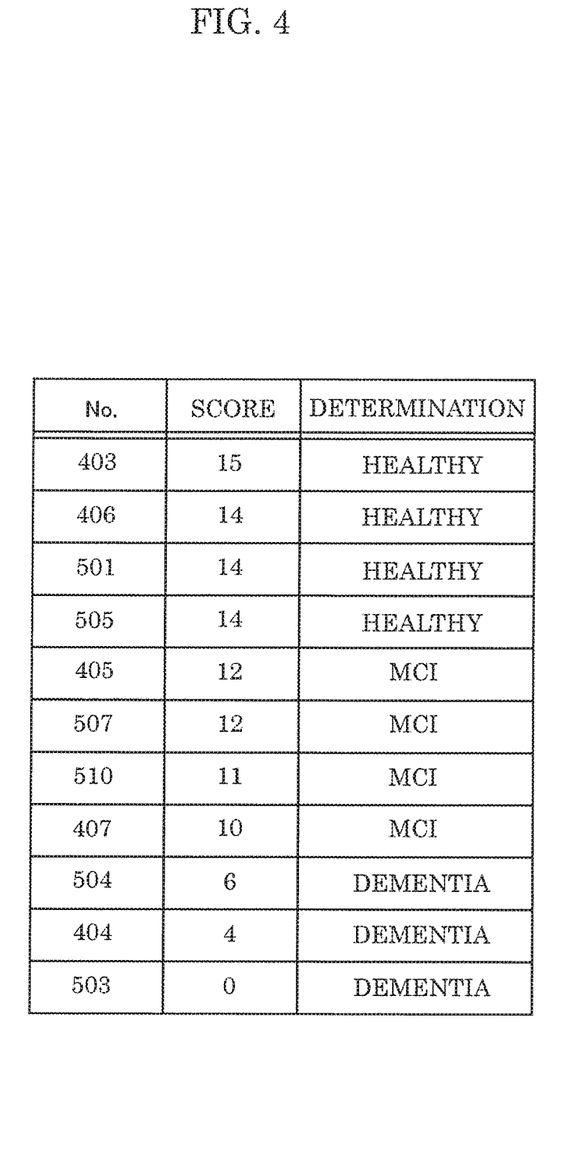
FIG. 4 is a diagram illustrating scores acquired by a person who underwent a forgetfulness counseling program.

FIG. 4 is a diagram illustrating scores acquired by people who underwent the forgetfulness counseling program.

The inventors gathered people including a healthy subject, a mild cognitive impairment patient (MCI patient), and a dementia patient, and conducted the forgetfulness counseling program. In the table illustrated in FIG. 4, the column denoted as No. indicates numbers arbitrarily assigned for identifying persons, the column denoted as SCORE indicates scores of the forgetfulness counseling program of the persons, and the column denoted as DETERMINATION indicates the results of determination of whether the persons are healthy subjects, MCI patients, or dementia patients. It should be noted that, in the table illustrated in FIG. 4, a person whose score is greater than or equal to 14 is determined as healthy (a healthy subject), a person whose score is from 7 to 13 is determined as having an MCI (an MCI patient), and a person whose score is less than or equal to 6 is determined as having dementia (a dementia patient).

In addition, for each of the persons who underwent the forgetfulness counseling program, reference data 151 that indicates a relationship between the total number of times of use of toilet 500 and a cognitive function of the person is generated, by obtaining an amount of electric power consumed by the person in toilet 500, and calculating a total number of times of use of toilet 500 based on the amount of electric power consumed that has been obtained.

For example, when evaluation unit 130 determines whether a subject is a healthy subject, or an MCI patient or a dementia patient, reference data 151 is the threshold (a predetermined threshold) of the total number of times of use of toilet 500 described above. Evaluation unit 130, for example, checks the total number of times of use of toilet 500 calculated by calculation unit 120 against reference data 151 including the threshold, and evaluates the subject as an MCI patient or a dementia patient when the total number of times of use of toilet 500 is less than or equal to the threshold, and as a healthy subject when the total number of times of use of toilet 500 is greater than the threshold.

Figure 5A:
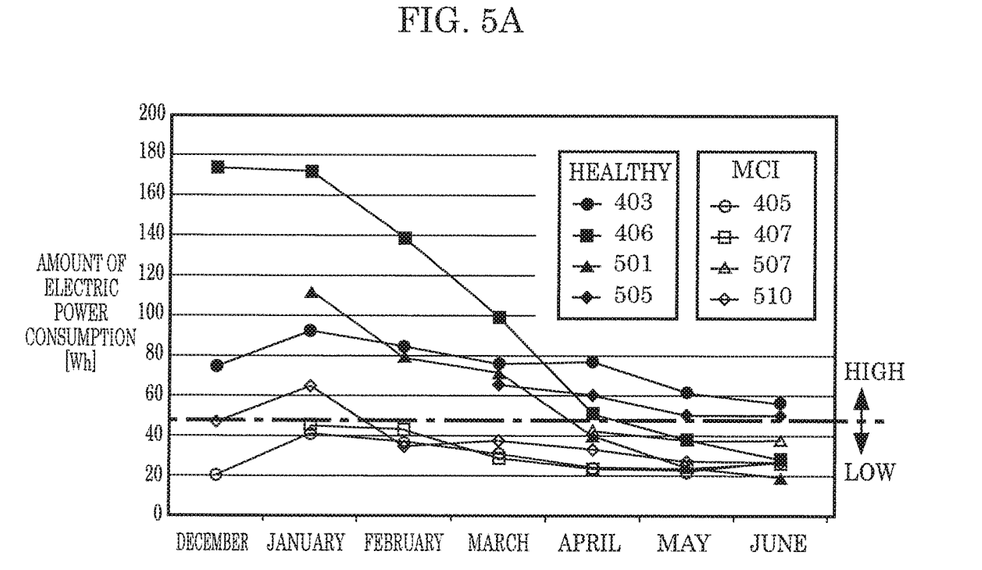
FIG. 5A is a polygonal line graph indicating, for each month, average values of amounts of electric power consumed in a toilet per day by healthy subjects and MCI patients.
Figure 5B:
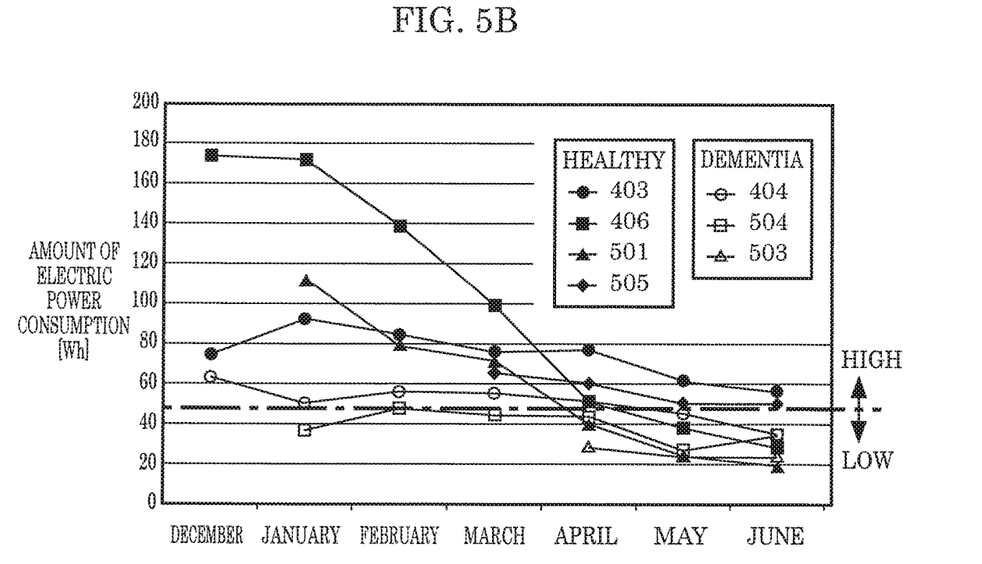
FIG. 5B is a polygonal line graph indicating, for each month, average values of amounts of electric power consumed in a toilet per day by healthy subjects and dementia patients.

FIG. 5A is a polygonal line graph indicating, for each month, average values of amounts of electric power consumed in toilet 500 per day by healthy subjects and MCI patients. FIG. 5B is a polygonal line graph indicating, for each month, average values of amounts of electric power consumed in toilet 500 per day by healthy subjects and dementia patients.

As illustrated in FIG. 5A and FIG. 5B, the average values, for each month, of the amounts of electric power consumed in toilet 500 per day by the MCI patients and the dementia patients are lower than those of healthy subjects. More specifically, the average values, for each month, of the amounts of electric power consumed in toilet 500 per day by the healthy subjects are higher than approximately 48 Wh. In contrast, the average values, for each month, of the amounts of electric power consumed in toilet 500 per day by the MCI patients and the dementia patients are lower than approximately 48 Wh. As described above, it is possible to determine whether a persons is a healthy subject, or an MCI patient or a dementia patient, by evaluating the average values, for each month, of the amounts of electric power consumed in toilet 500 per day.

Here, for example, if the amount of electric power consumption of a single use in toilet 500 is 8 Wh, a threshold of a total number of times of use of toilet 500 is 6 in the examples illustrated in FIG. 5A and FIG. 5B. In such a case, as reference data 151, for example, it is stored in storage unit 150 that the threshold of the total number of times of use of toilet 500 is 6. Furthermore, obtainment unit 110 obtains an amount of electric power consumed per day, that is the above-described predetermined period of time, as use information of toilet 500 by the subjects. Furthermore, calculation unit 120 calculates the total number of times of use of toilet 500 by the subject, based on the amount of electric power consumed that has been obtained by calculation unit 120. In addition, evaluation unit 130 evaluates the subject as a healthy subject when the total number of times of use of toilet 500 by the subject that has been calculated by calculation unit 120 exceeds 6 that is the threshold, and evaluates the subject as being suspected of having an MCI or dementia. Furthermore, output unit 140 outputs a result of the evaluation performed by evaluation unit 130 to notification device 400, for example.

In addition, the inventors conducted a significant difference test (t-test) for examining whether there is a significant difference between the healthy subjects and MCI patients, in the amounts of electric power consumed in toilet 500 per day for each month and the total amounts of electric power consumed in toilet 500 for each month. T-test is a test for determining whether averages are the same, on the assumption that two populations both follow a normal distribution. It should be noted that the level of significance is 0.05 according to the present embodiment.

Figure 6A:
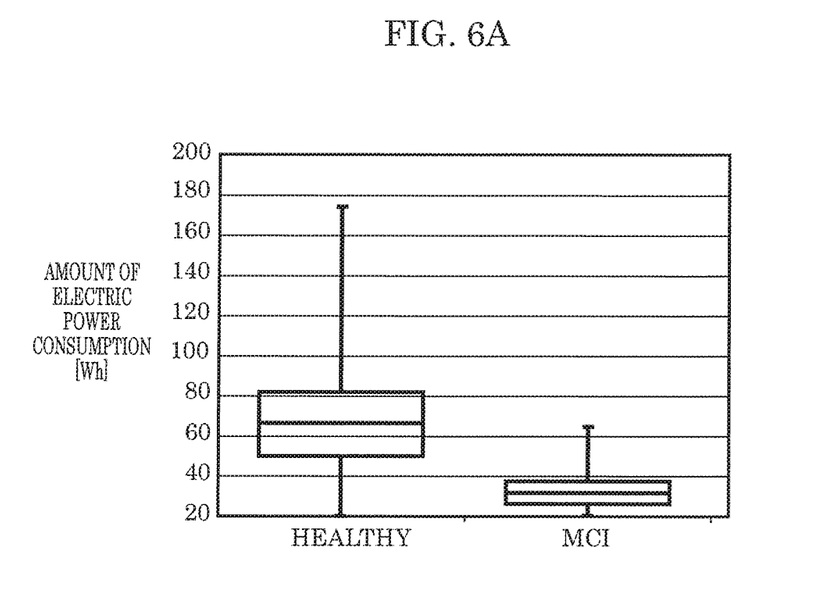
FIG. 6A is a graph indicating, in a boxplot, the amounts of electric power consumed in a toilet per day by healthy subjects and MCI patients, for each month.
Figure 6B:
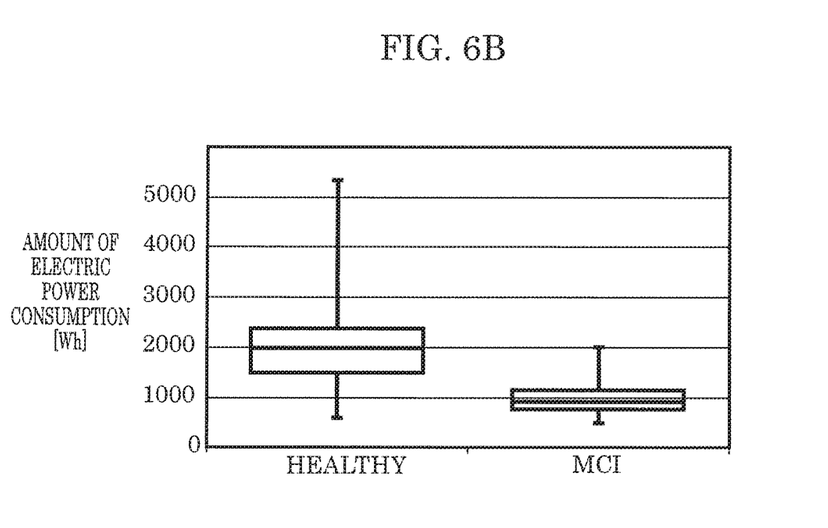
FIG. 6B is a graph indicating, in a boxplot, the total amounts of electric power consumed in a toilet by healthy subjects and MCI patients, for each month.

FIG. 6A is a graph indicating, in a boxplot, the amounts of electric power consumed in toilet 500 per day by healthy subjects and MCI patients for each month. FIG. 6B is a graph indicating, in a boxplot, for each month, the total amounts of electric power consumed in toilet 500 by healthy subjects and MCI patients.

When the amount of electric power consumed in toilet 500 per day for each month is compared between the healthy subjects and the MCI patients, p=0.00007279 where p is a probability that falls outside the 95% confidence interval. With this, it is possible to determine that there is a significant difference between the healthy subjects and the MCI patients in the amounts of electric power consumed in toilet 500 per day for each month.

In addition, when the total amount of electric power consumed in toilet 500 for each month is compared between the healthy subjects and the MCI patients, p=0.000033382 where p is a probability that falls outside the 95% confidence interval. With this, it is possible to determine that there is a significant difference between the healthy subjects and the MCI patients in the total amounts of electric power consumed in toilet 500 for each month.

Figure 6C:
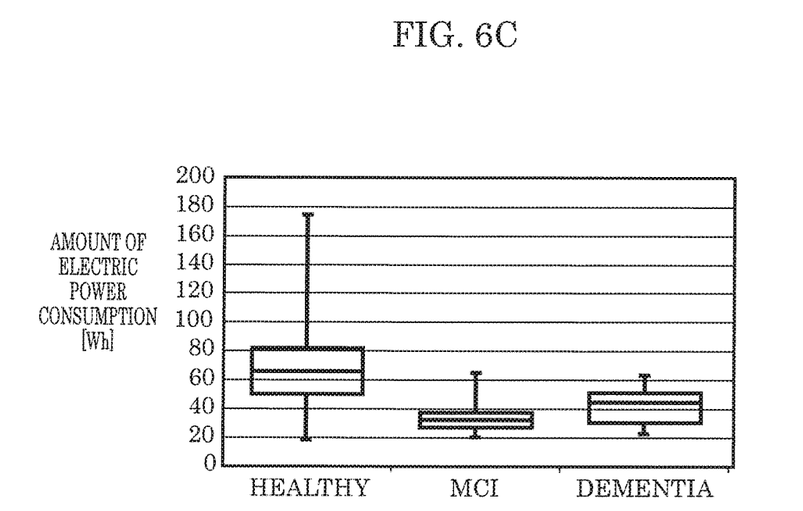
FIG. 6C is a graph indicating, in a boxplot, the amounts of electric power consumed in a toilet per day by healthy subjects, MCI patients, and dementia patients, for each month.

FIG. 6C is a graph indicating, in a boxplot, the amounts of electric power consumption of healthy subjects, MCI patients, and dementia patients in toilet 500 per day for each month.

As illustrated in FIG. 6C, there is a difference in the amount of electric power consumed in toilet 500 per day for each month between the healthy subjects and the dementia patients as well.

Here, in view of the fact that there are users of bladder control pads such as diapers (hereinafter referred to as pads) among persons who are suspected of an MCI or dementia, the inventors investigated whether there is a possibility that use of the pads affects a total number of times of use of toilet 500.

Figure 6D:
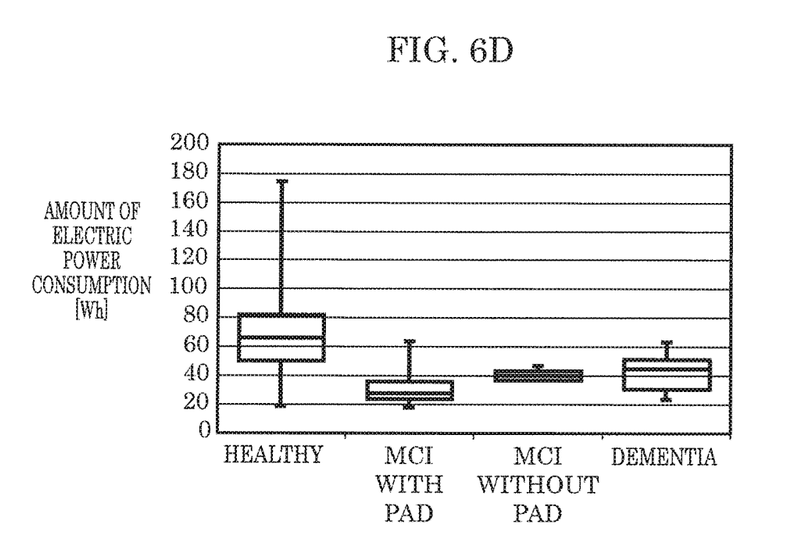
FIG. 6D is a graph indicating, in a boxplot, the total amounts of electric power consumed in a toilet for each month, in relation to the presence or absence of a pad.

FIG. 6D is a graph indicating, in a boxplot, total amounts of electric power consumed in toilet 500 for each month, in relation to using or not using a pad. It should be noted that a total number of subjects (N number) who are healthy subjects in FIG. 6D is 4, and a total number of pad users among the total number of subjects who are healthy subjects is 0. In addition, in FIG. 6D, the N number of MCI patients without a pad (MCI WITHOUT PAD indicated in FIG. 6D) is 3. In FIG. 6D, the N number of MCI patients with a pad (MCI WITH PAD indicated in FIG. 6D) is 1. In addition, a total number of subjects (N number) who are dementia patients in FIG. 6D is 3, and a total number of pad users among the total number of the subjects who are dementia patients is 3.

As illustrated in FIG. 6D, the subjects denoted as MCI WITHOUT PAD, MCI WITH PAD, and DEMENTIA, tend to be different from the healthy subjects and similar to one another, and are low in the amount of electric power consumption per day for each month. In addition, for example, the subjects denoted as MCI WITHOUT PAD tend to be similar to the subjects denoted as MCI WITH PAD and DEMENTIA, and a significant difference from the subjects denoted as MCI WITH PAD and DEMENTIA is not recognized. In other words, a difference in the total number of times of use of toilet 500 is shown between the healthy subjects and the MCI patients or the dementia patients, regardless of using or not using a pad. For that reason, it is shown that the causal factor of the difference in the total number of times of use of toilet 500 between the healthy subjects and the MCI patients or the dementia patients is not due to the pad but due to the degree of the cognitive function.

Figure 7A:
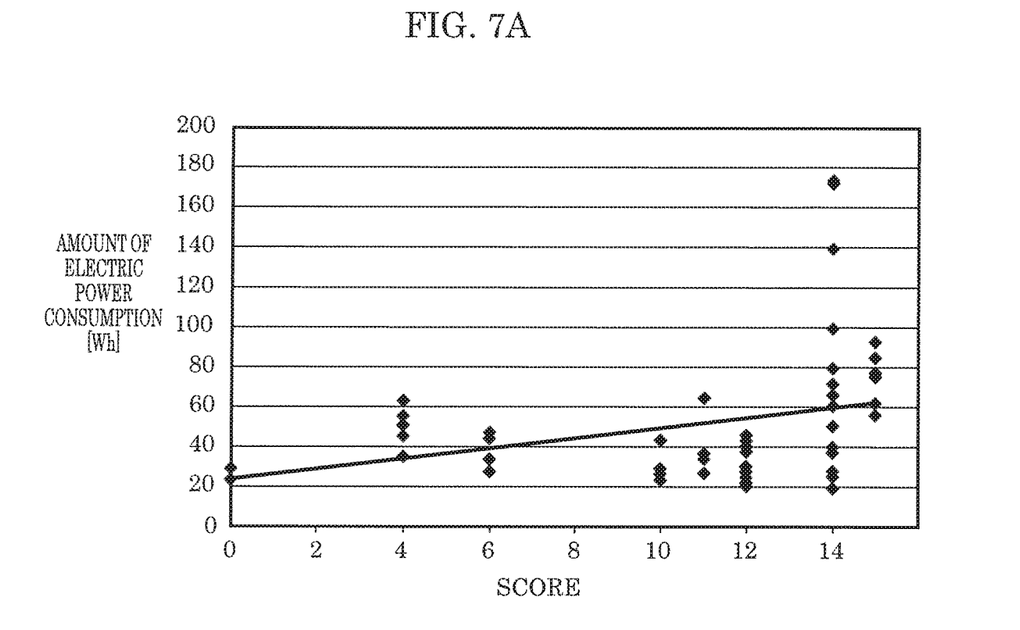
FIG. 7A is a diagram illustrating average values of amounts of electric power consumed per day for each month with respect to the scores of the forgetfulness counseling program.
Figure 7B:
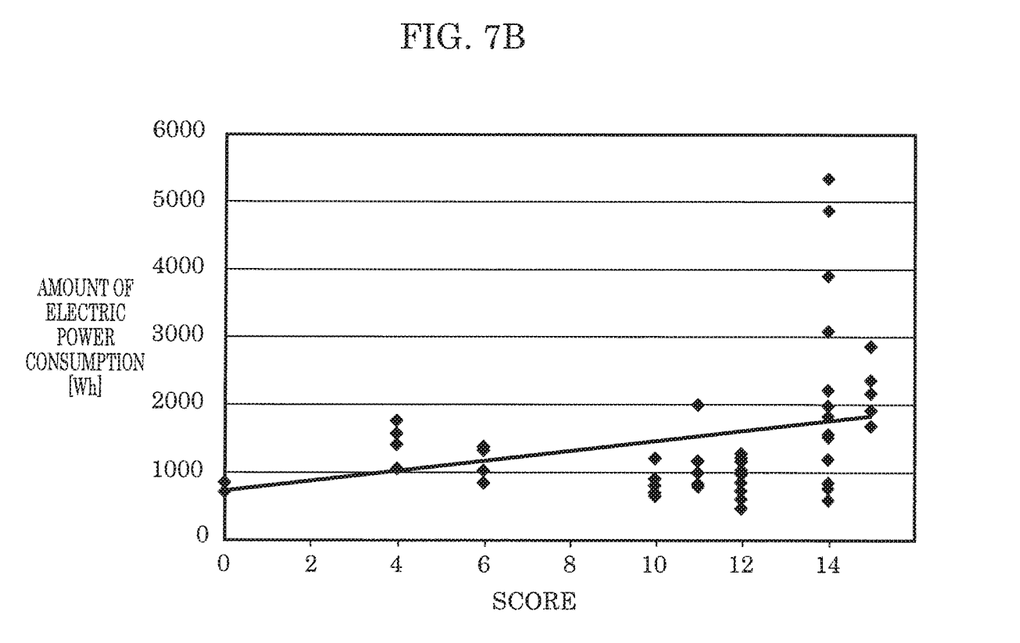
FIG. 7B is a diagram illustrating average values of total amounts of electric power consumed for each month with respect to the scores of the forgetfulness counseling program.

FIG. 7A is a diagram indicating an average value of the amount of electric power consumed per day for each month with respect to the scores of the forgetfulness counseling program. FIG. 7B is a diagram indicating average values of total amounts of electric power consumed for each month with respect to the scores of the forgetfulness counseling program. It should be noted that the number of plots of data indicated in FIG. 7A and FIG. 7B are each 60. In addition, the straight lines indicated in FIG. 7A and FIG. 7B are each a regression line calculated using the method of least square.

As illustrated in FIG. 7A, there is a positive correlation between the scores of the forgetfulness counseling program and the amount of electric power consumed per day for each month. The correlation coefficient is approximately 0.3376.

Likewise, as illustrated in FIG. 7B, there is a positive correlation between the scores of the forgetfulness counseling program and the total amount of electric power consumed for each month. The correlation coefficient is approximately 0.3336.

In view of the above, cognitive function evaluation device 100 may obtain, as use information of toilet 500 by a subject, an amount of electric power consumed per day for each month or a total amount of electric power consumed for each month, and evaluate, in a stepwise manner, the degree of a cognitive function of the subject, instead of determining whether the subject is a healthy subject, or an MCI patient or a dementia patient.

For example, although one threshold is held in reference data 151 in the above description, a total number of thresholds is not specifically limited. The total number of thresholds used as reference data 151 may be one, or two or more. For example, two thresholds may be used as reference data 151, and cognitive function evaluation device 100 may perform evaluation based on the two thresholds to determine whether a subject is a healthy subject, an MCI patient, or a dementia patient.

(Variation)

According to the foregoing embodiment, cognitive function evaluation device 100 calculates a total number of times of use of toilet 500 by a subject in a predetermined period of time, based on use information indicating a state of use of toilet 500 by the subject which has been detected by detection device 300, and evaluates the degree of a cognitive function. It has been described that detection device 300 is: electric power meter 551 that detects an amount of electric power consumed in toilet 500; water flowmeter 511 that detects an amount of water used in toilet 500; detection sensor 552 that detects an amount of use of toilet paper in toilet 500; or human detecting sensor 540.

Figure 8:
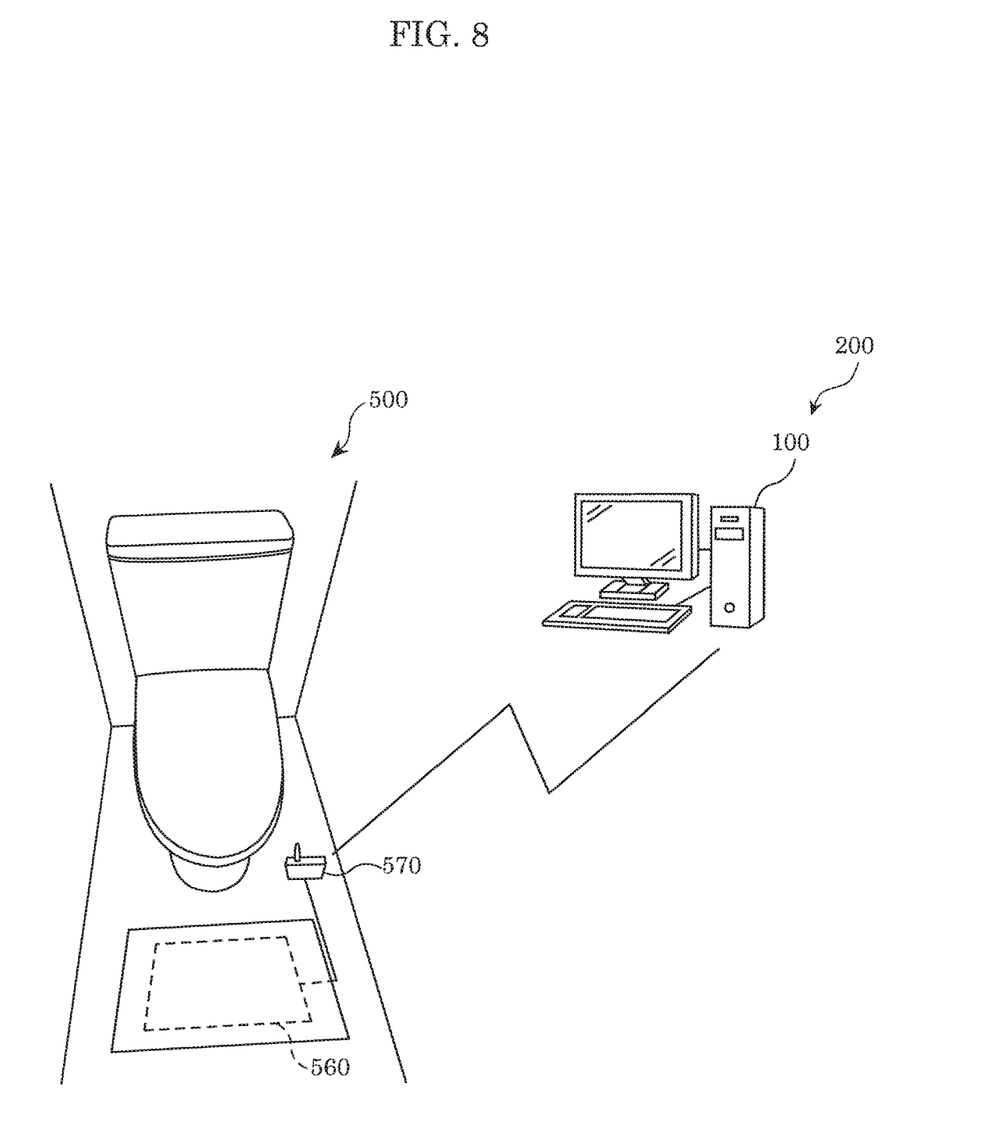
FIG. 8 is a diagram illustrating a configuration of a cognitive function evaluation system according to a variation of the embodiment.

FIG. 8 is a diagram illustrating a configuration of cognitive function evaluation system 200 according to a variation of the embodiment.

FIG. 8 illustrates pressure sensor 560 as another example of detection device 300.

Pressure sensor 560 is a sensor that detects a pressure. More specifically, pressure sensor 560 detects whether or not a subject has stepped on pressure sensor 560. In this manner, use information of toilet 500 by subject can also be detected by pressure sensor 560. In other words, pressure sensor 560 may be employed as detection device 300 instead of, for example, human detecting sensor 540 illustrated in FIG. 1. Pressure sensor 560 is connected to, for example, communication device 570.

Communication device 570 is a device that outputs, to cognitive function evaluation device 100, a change in a pressure detected by pressure sensor 560 as use information of toilet 500 by a subject. In the example illustrated in FIG. 8, communication device 570 is connected to cognitive function evaluation device 100 to be capable of performing radio communication with cognitive function evaluation device 100. In this case, obtainment unit 110 may include a radio communication module for performing the radio communication. With this configuration, cognitive function evaluation device 100 is capable of obtaining use information of toilet 500 by a subject without requiring large-scale equipment.

It should be noted that cognitive function evaluation system 200 may include two or more of electric power meter 551; water flowmeter 511; detection sensor 552; and human detecting sensor 540 illustrated in FIG. 1; and pressure sensor 560 illustrated in FIG. 8 as detection device 300. For example, cognitive function evaluation system 200 may include both of pressure sensor 560 and human detecting sensor 540.

In addition, pressure sensor 560 and cognitive function evaluation device 100 (specifically, obtainment unit 110) may be connected to each other in a wired manner without the interposition of communication device 570.

Advantageous Effects, Etc.

As described above, cognitive function evaluation device 100 according to the embodiment includes: obtainment unit 110 that obtains use information indicating a state of use of toilet 500 by a subject; calculation unit 120 that calculates a total number of times of use of toilet 500 by the subject, based on the use information obtained by obtainment unit 110; evaluation unit 130 that evaluates a cognitive function of the subject, based on the total number of times of use calculated by calculation unit 120; and output unit 140 that outputs a result of evaluation performed by evaluation unit 130.

According to the above-described configuration, with cognitive function evaluation device 100, it is possible to evaluate the degree of a cognitive function of the subject, based on a total number of times of use of toilet 500. Accordingly, with cognitive function evaluation device 100, it is possible to easily evaluate a cognitive function of the subject. In particular, with cognitive function evaluation device 100, it is possible to easily determine whether the subject is a healthy subject or a subject having an MCI whose cognitive function is decreased to the extent that no trouble is involved in daily life.

In addition, cognitive function evaluation device 100 is capable of notifying an asymptomatic dementia patient of the degree of a cognitive function, based on information obtained through normal daily activities performed by the subject. It is thus possible, for example, to urge a dementia patient to have an examination by a doctor. In other words, cognitive function evaluation device 100 is capable of assisting an asymptomatic dementia patient to have an examination by a doctor, by notifying the dementia patient of the degree of a cognitive function.

For example, evaluation unit 130 may evaluate a cognitive function of a subject whose total number of times of use of toilet 500 is lower than or equal to a predetermined threshold, to be lower than a cognitive function of a subject whose total number of times of use of toilet 500 is higher than the predetermined threshold.

As described above, the inventors have found that the total number of times of use of toilet 500 of MCI patients or dementia patients is lower than the total number of times of use of toilet 500 of healthy subjects. In view of the above, evaluation unit 130 compares the total number of times of use by a subject to a predetermined threshold, and thereby is capable of evaluating whether the subject is a person having a healthy cognitive function, or a person suspected of having an MCI or dementia.

In addition, for example, obtainment unit 110 may obtain, as use information, an amount of electric power consumed in toilet 500, an amount of water used in toilet 500, an amount of toilet paper used in toilet 500, or a total number of times of detection by human detecting sensor 540 in toilet 500.

By using these items of use information, calculation unit 120 is capable of easily calculating the total number of times of use of toilet 500 by the subject.

In addition, for example, cognitive function evaluation device 100 may include storage unit 150 that stores reference data 151 indicating a relationship between a total number of times of use of toilet 500 by a person and a cognitive function of the person. Evaluation unit 130 may evaluate a cognitive function of a subject by checking the total number of times of use of toilet 500 by the subject that has been calculated by calculation unit 120 against reference data 151 stored in storage unit 150.

In other words, cognitive function evaluation device 100 may perform communication with an external server device or the like in which reference data 151 is stored to evaluate a cognitive function of the subject, but may alternatively include storage unit 150 that is a storage device in which reference data 151 is stored. With this configuration, cognitive function evaluation device 100 is capable of evaluating a cognitive function of the subject without being connected to a network for communicating with an external server device. For that reason, convenience of cognitive function evaluation device 100 is improved.

In addition, cognitive function evaluation system 200 according to the embodiment includes cognitive function evaluation device 100, and detection device 300 that detects use information indicating a state of use of toilet 500 by a subject, and outputs the use information to obtainment unit 110 included in cognitive function evaluation device 100.

With this configuration, cognitive function evaluation system 200 is capable of evaluating the degree of a cognitive function of the subject, based on the total number of times of use of toilet 500. For that reason, according to cognitive function evaluation system 200, it is possible to easily evaluate a cognitive function of the subject. Furthermore, cognitive function evaluation system 200 is capable of notifying an asymptomatic dementia patient of the degree of a cognitive function, based on information obtained through normal daily activities performed by the subject. It is thus possible, for example, to urge a dementia patient to have an examination by a doctor. In other words, cognitive function evaluation system 200 is capable of assisting an asymptomatic dementia patient to have an examination by a doctor, by notifying the asymptomatic dementia patient of the degree of a cognitive function.

In addition, for example, detection device 300 may be: electric power meter 551 that detects an amount of electric power consumed in toilet 500; water flowmeter 511 that detects an amount of water used in toilet 500; detection sensor 552 that detects an amount of toilet paper used in toilet 500; or human detecting sensor 540.

By employing these devices as detection device 300, cognitive function evaluation system 200 is capable of easily calculating a total number of times of use of toilet 500 by a subject.

In addition, a cognitive function evaluation method performed by cognitive function evaluation device 100 according to the embodiment includes: obtaining use information indicating a state of use of toilet 500 by a subject; calculating a total number of times of use of toilet 500 by the subject, based on the use information that has been obtained in the obtaining; evaluating a cognitive function of the subject, based on the total number of times of use that has been calculated in the calculating; and outputting a result of evaluation performed in the evaluating.

In addition, the present invention may be implemented as a non-transitory computer-readable recording medium for use in a computer, the recording medium having a computer program recorded thereon for causing the computer to execute the steps included in the above-described cognitive function evaluation method.

With this, it is possible to evaluate the degree of a cognitive function of a subject, based on a total number of times of use of toilet 500. Accordingly, with such a program, it is possible to easily evaluate a cognitive function of a subject.

Other Embodiments

The cognitive function evaluation device, etc. according to the embodiment and the variation of the embodiment have been described above. However, the present invention is not limited to the above-described embodiment.

In the foregoing embodiment, Alzheimer's dementia has been described as one specific example of the symptom of a decrease in a cognitive function. However, a cognitive function indicates a capability of recognizing, memorizing, deciding, etc., and dementia is a symptom that shows a decrease in the above-described cognitive function. In other words, the degree of a cognitive function that is evaluated by the cognitive function evaluation device is not limited to the degree of Alzheimer's dementia, and may be, for example, the degree of vascular dementia, inebriety, and so on.

In addition, in the foregoing embodiment, data indicating a relationship between scores of the forgetfulness counseling program and a total number of times of use of toilet 500 by a person is stored in advance as reference data 151 in storage unit 150, in order to evaluate the degree of a cognitive function of a subject. However, reference data 151 is not limited to data indicating the relationship between the scores of the forgetfulness counseling program and the total number of times of use of toilet 500, as long as it is data that is used to be checked with the total number of times of use of toilet 500 so as to evaluate the degree of the cognitive function. For example, reference data 151 may be data indicating a relationship between the score of Montreal Cognitive Assessment (MoCA) test, Mini-Mental State Examination (MMSE), etc. and the total number of times of use of toilet 500.

In addition, although the above-described embodiment includes the descriptions of "greater than the threshold", "less than or equal to the threshold", and the like, these descriptions are not used in a strict sense. For example, the descriptions of "greater than a threshold" may indicate that it is greater than or equal to a threshold. Furthermore, when the descriptions of "greater than the threshold" and "less than or equal to the threshold" are used in a contrast manner, these descriptions may indicate that differentiation is made at the threshold, and respectively mean "greater than or equal to the threshold" and "less than the threshold".

In addition, the present invention can be implemented not only as the cognitive function evaluation device and the cognitive function evaluation system, but also as: a program that includes, as steps, processes performed by each of the structural components of the cognitive function evaluation device and the cognitive function evaluation system; and a computer readable recording medium that stores the program, such as a flexible disk, a hard disk, a CD-ROM, an MO, a DVD, a DVD-ROM, a DVD-RAM, a BD (Blu-ray (registered trademark) Disc), a semiconductor memory, etc. In addition, the program may be distributed via a communication network such as the Internet.

In other words, the above-described general and specific aspects may be implemented using a system, an apparatus, an integrated circuit, a computer program, or a computer-readable recording medium, or any combination of systems, apparatuses, integrated circuits, computer programs, or computer-readable recording media. For example, each of the structural components included in the cognitive function evaluation device need not be disposed in a single casing, and may respectively be disposed at different locations as long as the structural components are connected to be capable of transmitting and receiving various data items.

Moreover, aspects obtained through various modifications applied to the embodiment which may be conceived by a person skilled in the art as well as aspects realized by arbitrarily combining the structural components and functions of the embodiment without materially departing from the principles and spirit of the present invention are also included in the present invention.

The invention claimed is:

1. A system for performing an evaluation relating to a cognitive state of a subject, the system comprising:
    a toilet capable of usage by a subject;
    one or more detection devices operably coupled to the toilet, the one or more detection devices comprising at least one of:
        an electric power meter configured to measure electric power used by the toilet and output electric power meter data; and
        a water flow meter configured to measure water flow used by the toilet and output water flow meter data;
    one or more computer processors operably coupled to the one or more detection devices, the one or more computer processors configured to:
        obtain a usage information regarding use of a toilet by the subject, the usage information including at least one of the electric power meter data or water flow meter data corresponding to the toilet;
        calculate a total number of times of usage of the toilet by the subject based on the usage information, wherein one time of use, from the total number of times of use, of the toilet corresponds to (a) a change in electric power consumption as reflected in the electric power meter data, (b) a threshold amount of electric power consumption as reflected in the electric power meter data, (c) a change in water consumption as reflected in the water flow meter data, or (d) a threshold amount of water flow as reflected in the water flow meter data;
        evaluate a cognitive function of the subject based on the total number of times of use of the toilet, wherein where the total number of times of use of the toilet is lower than or equal to a predetermined threshold the cognitive function of the subject is evaluated as lower than cognitive function of a subject whose total number of times of use of a toilet is higher than the predetermined threshold; and
        output a result of the evaluation.

2. The system for performing an evaluation relating to a cognitive state of a subject according to claim 1, wherein at least one processor of the one or more computer processors is configured to obtain, as the usage information, one of an amount of electric power consumed in a toilet, an amount of water used in a toilet, an amount of toilet paper used in a toilet, and a total number of times of detection by a human detecting sensor in a toilet.

3. The system for performing an evaluation relating to a cognitive state of a subject according to claim 1, wherein at least one processor of the one or more computer processors is configured to:
    indicate a relationship between a total number of times of use of a toilet by a person and a cognitive function of the person, wherein:
    the cognitive function of the person is evaluated by checking the total number of times of use of the toilet by the person against the relationship.

4. A system comprising:
    a toilet capable of usage by a subject;
    a detection device coupled with the toilet, wherein the detection device obtains a usage information of the toilet, the usage information based on output of at least one of an electric power meter data or a water flow meter data corresponding to the toilet;
    a computer coupled to the toilet and the detection device, the computer capable of receipt of the usage information for evaluation of a cognitive function of the subject, wherein the computer is configured to:
        calculate a total number of times of use of the toilet by the subject, based on the usage information, wherein one time of use, from the total number of times of use of the toilet corresponds to (a) a change in electric power consumption as reflected in the electric power meter data, (b) a threshold amount of electric power consumption as reflected in the electric power meter data, (c) a change in water consumption as reflected in the water flow meter data, or (d) a threshold amount of water flow as reflected in the water flow meter data; and
        determine that, where the total number of times of use of the toilet is lower than or equal to a predetermined threshold, a cognitive function of the subject is evaluated as lower than a cognitive function of a subject whose total number of times of use of a toilet is higher than the predetermined threshold.

* * * * *